United States Patent
Castillo et al.

(10) Patent No.: US 7,892,584 B2
(45) Date of Patent: Feb. 22, 2011

(54) ONLINE, CONTINUOUS SENSOR AND METHOD FOR CURD MOISTURE CONTENT CONTROL IN CHEESE MAKING

(75) Inventors: Manuel Castillo, Lexington, KY (US); Colette C. Fagan, Glasnevin (IE); Colm P. O'Donnell, Clonskeagh (IE); Donal J. O'Callaghan, Whites Cross (IE); Frederick Alan Payne, Lexington, KY (US)

(73) Assignees: University College Dublin, National University of Ireland, Belfield, Dublin (IE); University of Kentucky Research Foundation, Lexington, KY (US); Teagase-The Agriculture & Food Development Authority, Fermoy, Co. Cork (IE)

( * ) Notice: Subject to any disclaimer, the term of this patent is extended or adjusted under 35 U.S.C. 154(b) by 482 days.

(21) Appl. No.: 12/109,650

(22) Filed: Apr. 25, 2008

(65) Prior Publication Data
US 2008/0268110 A1 Oct. 30, 2008

Related U.S. Application Data

(60) Provisional application No. 60/913,941, filed on Apr. 25, 2007.

(51) Int. Cl.
*A01J 25/06* (2006.01)
*G01N 21/49* (2006.01)
(52) U.S. Cl. .......... 426/36; 426/231; 426/248; 426/582; 426/518; 356/326; 356/342
(58) Field of Classification Search ............. 426/34–43, 426/231, 237, 248, 582, 518, 495; 356/300, 356/326, 342
See application file for complete search history.

(56) References Cited

U.S. PATENT DOCUMENTS 2,752,815 A 7/1956 Batchelor (Continued)

FOREIGN PATENT DOCUMENTS

FR 2680079 A1 * 2/1993

OTHER PUBLICATIONS

Castillo, M., Payne, F.A., Lopez, M.B., Ferrandini, E., Laencina, J. 2005. Preliminary Evaluation of an Optical Method for Modeling the Dilution of Fat Globules in Whey During Synergesis of Cheese Curd. Applied Engineering in Agriculture, vol. 21(2): 265-269.

(Continued)

*Primary Examiner*—Drew E Becker
(74) *Attorney, Agent, or Firm*—King & Schiekli, PLLC (57) ABSTRACT

A method is provided for improving quality of cheese produced from a milk batch. A light beam from an incident light source impinges onto a surface of the milk batch, and light backscatter is optically detected during a coagulation process and correlated to an optimum cutting time for the milk coagulum. Next, light backscattered from a curd and whey mixture derived from the milk batch during a syneresis process is optically detected and correlated to an optimum syneresis endpoint. At least one of the backscattered light data, optical parameters developed from analysis of the backscattered light data, and whey fat dilution are correlated to at least one of a milk protein %, a milk fat %, a milk total solids content, a milk processing temperature, a curd moisture content, a curd moisture change over time, whey fat content, a whey fat loss, and a final curd yield.

16 Claims, 5 Drawing Sheets

U.S. PATENT DOCUMENTS

| | | | |
|---|---|---|---|
| 4,144,804 A | | 3/1979 | O'Keefe et al. |
| 4,359,638 A | | 11/1982 | Allport |
| 4,497,898 A | | 2/1985 | Anderson et al. |
| 4,521,433 A | * | 6/1985 | Linklater et al. ............. 426/36 |
| 4,542,645 A | | 9/1985 | Richardson et al. |
| 4,986,660 A | | 1/1991 | Corbett |
| 5,009,794 A | | 4/1991 | Wynn |
| 5,137,738 A | | 8/1992 | Wynn |
| 5,172,193 A | * | 12/1992 | Payne et al. ................ 356/445 |
| 5,273,765 A | | 12/1993 | Weber |
| 5,403,552 A | | 4/1995 | Pardikes |
| 5,751,424 A | | 5/1998 | Bostater, Jr. |
| 5,912,730 A | | 6/1999 | Dahm et al. |
| 5,955,128 A | | 9/1999 | Bayevsky et al. |
| 5,983,709 A | | 11/1999 | O'Keefe |
| 6,052,184 A | | 4/2000 | Reed |
| 6,111,653 A | | 8/2000 | Bucknell et al. |
| 6,147,502 A | | 11/2000 | Fryer |
| 6,315,955 B1 | | 11/2001 | Klein |
| 6,721,054 B1 | | 4/2004 | Spooner |
| 6,753,966 B2 | | 6/2004 | Von Rosenberg |
| 6,795,183 B2 | | 9/2004 | O'Keeffe |
| 6,831,741 B1 | * | 12/2004 | De Kruif et al. ............ 356/338 |
| 6,836,325 B2 | | 12/2004 | Maczura |
| 6,963,403 B2 | | 11/2005 | Nagarajan et al. |
| 6,992,771 B2 | | 1/2006 | Bond et al. |
| 7,092,084 B2 | * | 8/2006 | Payne ........................ 356/246 |
| 7,217,234 B2 | | 5/2007 | Zettier |
| 2003/0030809 A1 | | 2/2003 | Boas |
| 2003/0098969 A1 | * | 5/2003 | Katz et al. .................... 356/73 |
| 2005/0233037 A1 | | 10/2005 | Bendtsen et al. |
| 2006/0044558 A1 | | 3/2006 | Furukawa |
| 2006/0057249 A1 | * | 3/2006 | Bell et al. ..................... 426/36 |
| 2007/0014893 A1 | * | 1/2007 | Misson et al. ................ 426/36 |
| 2008/0270063 A1 | * | 10/2008 | Everard et al. .............. 702/108 |
| 2009/0255473 A1 | * | 10/2009 | Katz et al. ............... 119/14.08 |

OTHER PUBLICATIONS

Castillo, M., Payne, F.A., Fagan, C.C., Leedy, M., O'Donnell, C.P., O'Callaghan, D.J., Feb. 2006. Backscatter of Near Infrared Light as an Instrument to Improve Control of Curd Moisture Content During Cheese Manufacturing. International Scholar Poster Session. Poster. Department of Biosystems and Agricultural Engineering, University of Kentucky.

Castillo, M., Payne, F.A., Mengue, M.P., Mar. 30, 2005. Simultaneous Monitoring of Coagulation and Syneresis in Cheese Processing Using Light Backscatter. Third Annual Kentucky Innovation and Enterprise Conference. Poster. Louisville, Kentucky, USA.

Castillo, M., Payne, F.A., Mengue, M.P., Leedy, M.A. Feb. 24, 2005. Novel Optical Sensor Technology for Simultaneous Monitoring of Coagulation and Syneresis in Cheese Processing. Poster. Lexington, Kentucky, USA.

Castillo, M., Payne, F.A., Mengue, M.P. Mar. 3, 2004. Syneresis Sensor Technology Development for Curd Moisture Content Control. Second Annual Kentucky Innovation and Enterprise Conference. Poster. Lexington, Kentucky, USA.

Castillo, M., Payne, F. A., Mengue, M.P. Apr. 14, 2004. Large Field of View Light Backscatter Sensor for Monitoring Whey Syneresis and Control Curd Moisture Content. Second International Scholar Poster Session. Poster. Lexington, Kentucky, USA.

Castillo, M., Payne, F.A., Lopez, M.B., Ferrandini, E., Laencina, J. 2005. Optical Sensor Technology for Measuring Whey Fat Concentration in Cheese Making. Journal of Food Engineering. 71: 354-360.

Castillo, M., Payne, F., Lopez, M.B., Ferrandini, E., Laencina, J., 2004. Kinetics of Synersis During Goats' Cheese Manufacturing. In Actas del 9th International Congress on Engineering and Food.

Castillo, M., Payne, F., Lopez, M.B., Ferrandini, E., Laencina, J. 2004. Development of a Fiber Optic Sensor to Measure Low Fat Concentration in Goats' Whey. In Actas del 9th International Congress on Engineering and Food.

Castillo, M., Payne, F.A., Lopez, M.B., Laencina, J. 2005. Optical Sensors to Monitor and Control the Processing of Goat Cheese. in Special Issue of Dairy Federation 0501/Part 4; pp. 250-256. Ed. International Dairy Federation.

Castillo, M., payne, F.A., Shea, A. Jul. 24-28, 2005. Development of a Combined Sensor Technology for Monitoring Coagulation and Syneresis Operations in Cheese Making. ADSA Annual Meeting. Poster. Cincinnati, Ohio, USA.

U.S. Appl. No. 11/789,197 Notice of Allowance Nov. 9, 2010.

* cited by examiner

ONLINE, CONTINUOUS SENSOR AND METHOD FOR CURD MOISTURE CONTENT CONTROL IN CHEESE MAKING

This utility patent application claims the benefit of priority in U.S. Provisional Patent Application Ser. No. 60/913,941 filed Apr. 25, 2007, the entire disclosure of which is incorporated herein by reference.

This invention was made with at least partial support under Grant No. NRI-USDA 2005-35503-15390. The Government may have certain rights in this invention.

TECHNICAL FIELD

The present invention generally relates to the cheese making art and, more particularly, to a method of improving the quality of cheese produced from a curd and whey mixture by monitoring coagulation and syneresis using a large field of view sensor.

BACKGROUND OF THE INVENTION

The first major step in the cheese making process is the coagulation of the milk, such as by enzymatic hydrolysis of κ-casein. To achieve this end, enzyme extracts from calf stomachs, microbially produced enzymes, or other enzyme sources are utilized. The hydrolysis of κ-casein leads to destabilization of the colloidal system of the milk. This is followed by aggregation of the micelles into clusters. Over time, the clusters grow in size. This growth in size is followed by cross-linking between chains which eventually transform the milk into a gel or coagulum. Once a desired endpoint is reached in the coagulation process, the coagulum is "cut," for example by traversing with wire knives to slice the coagulum into cubes. Accurate prediction of the optimal cutting time is an important factor in consistent, batch-to-batch quality and moisture content in the final cheese product.

The second major step in cheese making is syneresis, which initiates immediately following the coagulum cutting step. Syneresis is the phase separation process in cheese making that follows the cutting of the milk coagulum into cubes. Syneresis is generally promoted by thermal and/or mechanical treatments (cutting), and also may be slightly influenced by use of additives such as calcium chloride. During syneresis, rearrangement of the casein network, which constitutes the gel matrix, causes the shrinkage of the curd matrix and results in expulsion of whey from the curd grains, resulting in a solid:liquid mixture whose proportions change over time as syneresis endpoint nears.

Syneresis control influences cheese quality and yield as a result of its effects on moisture, mineral and lactose content of the curd. Syneresis also influences protein and fat losses in whey, which in turn affects cheese yield.

Curd syneresis is a kinetically complex process. Currently, there are no suitable techniques for reliably and reproducibly measuring syneresis as a means for studying and monitoring the syneresis process, particularly techniques adaptable to online, automated monitoring systems. The majority of techniques can be classed as either separation or dilution methods. Each method presents unique drawbacks.

At present, in the cheese industry worldwide, syneresis is empirically controlled by vat temperature, milk pH, stirring speed and time, depending on cheese type and the cheese maker's preferences. Unfortunately, inadequate curd moisture control resulting from such empirical process controls can lead to heterogeneous cheese ripening and quality, rather than providing homogenous conditions leading to a consistent end product from batch to batch. Better control of syneresis would give more consistent curd moisture content and pH, and more consistent curd concentration of minerals and lactose at the beginning of the curing process, resulting in a more homologous quality of product from batch to batch.

The present invention relates to a method of improving the quality of cheese produced from a curd and whey mixture. More specifically, the present method provides improved monitoring of both milk coagulation and curd syneresis during cheese making. Even more, the method and sensor are easily adapted for continuous, online monitoring of the cheese making process from initiation of coagulation to syneresis endpoint, and also prediction of endpoints for both processes, allowing better control of the entire cheese making process to ensure moisture content consistency and better cheese quality.

SUMMARY OF THE INVENTION

In accordance with the foregoing need identified in the ale as described herein, in one aspect there is provided a method of improving quality of cheese produced from a milk batch, comprising the steps of impinging a light beam from an incident light source onto a surface of the milk batch, and optically detecting light backscattered from said milk batch during a coagulation process to collect light backscatter data. Those light backscatter data are correlated to an optimum cutting time whereby a syneresis process is initiated. Next is the step of optically detecting light backscattered from a biphasic curd and whey mixture derived from that milk batch during the syneresis process, and correlating that light backscatter data to an optimum syneresis endpoint. The light backscatter data, optical parameters developed from analysis of the light backscatter data, and/or whey fat dilution may be correlated to at least one of said backscattered light data, optical parameters developed from analysis of the backscattered light data, and whey fat dilution to at least one of a milk protein %, a milk fat %, a milk total solids content, a milk processing temperature, a curd moisture content, a curd moisture change over time, whey fat content, a whey fat loss, and a final curd yield. Advantageously, the present method is predictive, not only of an optimal cutting time during a coagulation process, but also of an optimum syneresis endpoint after collection of light backscatter data for about 15 minutes following the cutting step which initiates syneresis.

In one embodiment, the steps of impinging the light beam, optically detecting light backscattered from the milk batch during the coagulation process, and optically detecting light backscattered by the milk batch during the syneresis process are accomplished by providing a light guide for guiding the light beam onto the milk batch surface, with the light guide having a diameter of about 0.2 inches, and providing a light collector for collecting backscattered light reflected from the milk batch surface, with the light collector having a diameter of about 0.2 inches. The light guide and the light collector are separated by a distance of about 0.4 inches to about 0.6 inches. The light source may emit light at a wavelength of from about 950 nm to about 1000 nm. An optical detector receives light from the light collector for further processing.

In another aspect, there is provided a method of predicting an optimum endpoint for a syneresis process in a cheese making process. The method comprises impinging a light beam from an incident light source onto a surface of a biphasic curd and whey mixture derived from a milk batch, and optically detecting light backscattered from said curd and whey mixture during the syneresis process. The collected light backscatter data are correlated to an optimum syneresis endpoint. Equations predictive of the optimum syneresis endpoint are provided, which equations include parameters selected from at least one of a milk protein % parameter, a milk fat % parameter, a milk total solids content parameter, a milk processing temperature parameter, a curd moisture content parameter, a curd moisture change over time parameter, a whey fat content parameter, a whey fat loss parameter, and a final curd yield parameter. A sensor is provided for accomplishing the method.

In the following description there are shown and described several different embodiments of this invention, simply by way of illustration of some of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated herein and forming a part of the specification, illustrate several aspects of the present invention and together with the description serve to explain certain principles of the invention. In the drawings.

Reference will now be made in detail to the present preferred embodiments of the invention, examples of which are illustrated in the accompanying drawings.

DETAILED DESCRIPTION OF THE INVENTION

In accordance with the purposes of the present invention as described herein, a method is provided for improving the quality of cheese produced from a milk sample. The method comprises the steps of: (1) optically monitoring the milk during the coagulation process; (2) optically monitoring the curd and whey mixture during the subsequent syneresis process; (3) predicting an optimal coagulum cutting time based on that coagulation monitoring; and (4) predicting an optimal syneresis endpoint based on that syneresis monitoring in optional combination with that coagulation monitoring and also optionally with certain milk composition variables (e.g., milk fat, protein fat ratio, and the like) and operating parameters (e.g., temperature), thereby allowing maximizing of curd yield and minimizing whey fat loss. In this manner, such optical monitoring steps allow production of a cheese curd with a consistent moisture content, batch to batch. The monitoring step includes directing light from a large field of view sensor 10 onto a surface of the milk or curd and whey mixture, in accordance with whether milk coagulation or curd syneresis is being monitored during the cheese making process, and detecting light backscattered from that surface.

EXAMPLE 1

Figure 1:
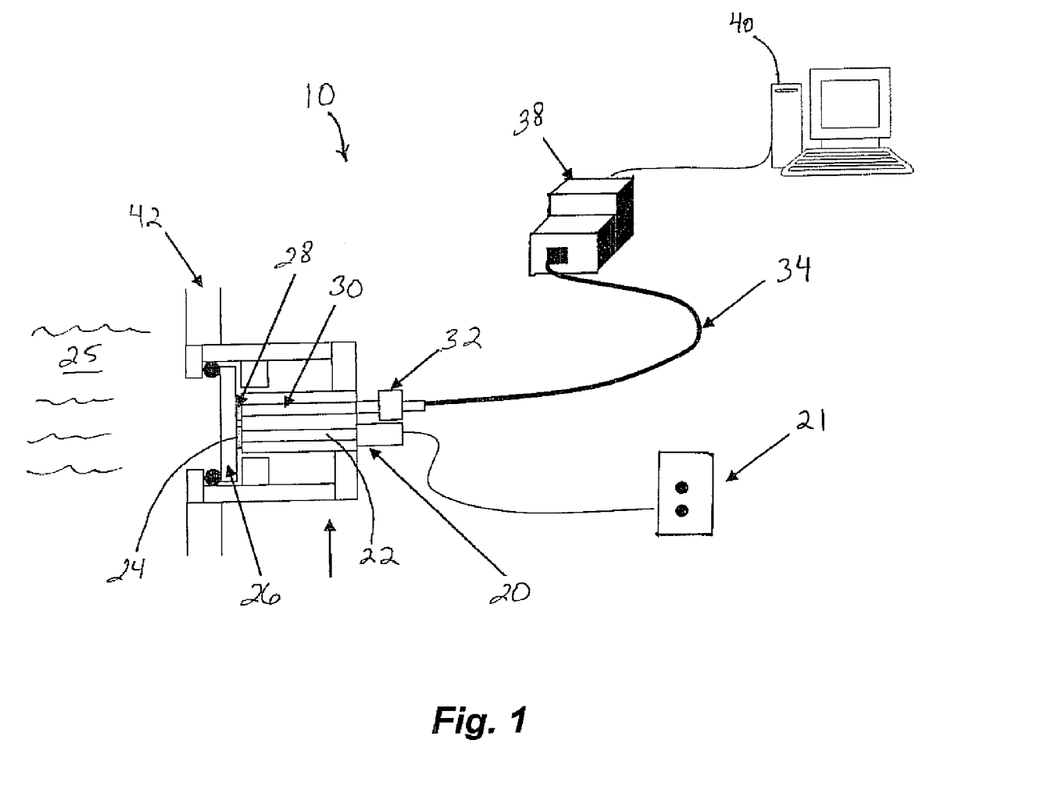
FIG. 1 schematically depicts a large field of view (LFV) sensor and optical configuration for monitoring coagulation and syneresis in a cheese making process.

As shown schematically in FIG. 1, a large field of view (LFV) sensor 10 was provided having a light source 20 (in the depicted embodiment, a tungsten halogen light source having a spectral range of 360-2000 nm). The light source 20 is powered by a power supply 21.

Light from the light source 20 was directed through a light guide 22, in the depicted embodiment an optical fiber, and optionally through a vertical polarizing plate 24, and a large-diameter glass window 26 to impinge on a milk sample 25. The large-diameter glass window 26 allowed scattered light to be collected from a large area. An optional second polarizing plate 28 allowed selective detection of horizontally polarized light. Collected backscattered light was transmitted through a light collector 30 (in the depicted embodiment, a second optical fiber), a SMA connector 32, and a fiber optic cable 34 (~800 μm diameter fiber optic cable; Spectran Specialty Optics, Avon, Conn., USA) to the master unit of a dual miniature fiber optic spectrometer 38 (model SD2000, Ocean Optics, Inc., Dunedin, Fla., USA).

In the depicted embodiment, near-infrared light was impinged on a milk sample to be monitored at a wavelength of from about 970 nm to about 990 nm (average of 980 nm). First (light transmitting) and second (backscattered light collecting) optical fibers 22, 30 were provided having 0.200 inch diameters, with first and second optical fibers 92, 30 being spaced 0.516 inches apart (centerline to centerline), facilitating transmission of light. This was hypothesized to be important, particularly during syneresis, due to progressively decreasing light backscatter from the curd:whey mixture over time. Thus, an increased transmission/collection area was evaluated to compensate for the decreasing signal during syneresis.

The spectrometer 38 master unit had a 25 μm slit, a 300 lines $mm^{-1}$ diffraction grating with a range of 300-2000 nm and a detection bandwidth of 200 to 1100 nm. The unit was equipped with a 2048-pixel linear CCD-array silicon detector (Sony ILX 511, Tokyo, Japan) with a response range of 200 to 1100 nm and a sensitivity of 86 photons per count at 1 s integration time. Spectra were collected over the range 300 nm to 1100 nm with a resolution of 0.7 μm.

Light emerging from the fiber optic cable was processed in the spectrometer and data were transferred to a computer 40 through an A/D converter. The integration time was set to 7 s by the computer 40 software (OOIBase, Version 1.5, Ocean Optics, Inc.). Each spectral scan was automatically processed by subtracting the dark background spectral scan. Each spectral scan was reduced to 38 averages by dividing them into 20 nm wavebands with mid-wavelengths of 340+20·n ($1 \leq n \leq 38$) giving 38 wavebands in the range (360-1100 nm) and averaging the optical response for the wavelengths constituting each waveband. The voltage readings (sensor output) for the first min of data were averaged within each waveband to calculate the initial voltage response, $V_0$. The voltage intensity at every waveband, V was divided by its corresponding $V_0$ to obtain the light backscatter ratio, R. The first derivative, R' of the light backscatter ratio profile was calculated by conducting linear least-squares regression on the most recently collected 4 min of data, if $t^*_{max}$ was $\leq 8$ min or the most recently collected 5 min of data, if $t^*_{max}$ was >8 min. This was because the sensor response at low milk temperatures, i.e. those experiments with $t^*_{max}$>8 min, contained a greater degree of noise and a 5 min interval was required to smooth the R' profile. The calculated slope was assigned to the midpoint of the data subset used. The second derivative (R") was calculated in a similar manner but using 60 data points to smooth the R" profile.

As shown in FIG. 1, the sensor 10 of the present invention was adapted to be secured to a suitable cheese making vessel, such as via a port traversing a portion of a cheese making vat wall 42. Conveniently, this provided a mechanism whereby the cheese making process could be monitored intermittently or continuously for a portion or an entirety thereof. Thus, the method and LFV sensor 10 of the present invention may be adapted for continuous, online monitoring of the cheese making process to allow monitoring and control of both the coagulation and syneresis processes from start to finish.

EXAMPLE 2

Milk coagulation tests were conducted over a broad range of conditions typically used in the cheese making industry. A three-factor, filly randomized, spherical, central composite design (CCD) was employed to evaluate the response of the proposed syneresis sensor prototype over a wide range of coagulation and syneresis rates. The CCD consisted of a $2^k$ factorial (k=3) with 2k axial points and six center points (i.e., 20 runs in total) and was carried out in triplicate. The three factors selected as independent variables were coagulation temperature (T), calcium chloride ($CaCl_2$) addition level (CCAL) and cutting time ($t_{cut}$). The experimental factors, their selected levels and coded values are presented in Table 1.

TABLE 1

The experimental factors and levels employed in the central composite rotatable experimental design

| Factors (Coded value) | Temperature (° C.) | Added $CaCl_2$ (mM) | Cutting time (β) (dimensionless)[a] |
|---|---|---|---|
| −1.682 | 23.6 | 0.318 | 1.32 |
| −1 | 27.0 | 1.00 | 1.80 |
| 0 | 32.0 | 2.00 | 2.50 |
| 1 | 37.0 | 3.00 | 3.20 |
| 1.682 | 40.4 | 3.68 | 3.68 |

[a]Experimental cutting time levels were selected as $\beta \cdot t^*_{max}$, where $t^*_{max}$ was the time from enzyme addition to the inflection point of the light backscatter profile obtained using a CoAguLite ™ sensor.

Unpasteurized and unhomogenized milk was obtained from a local milk processing plant. Milk was pasteurized at 65° C. for 30 min and rapidly cooled to 2° C. A 40 mL sample of milk was removed for compositional analysis, using a MilkoScan FT 120 (Foss Electric, Denmark), and a further 7.20 kg of the milk was weighed for use in each experiment. $CaCl_2$ at the required level was added to the 7.20 kg of milk and stirred for 3 min then left to equilibrate for 30 min in a cold room at 2° C. Milk was adjusted in the cold room to a pH of 6.51 using an experimentally obtained linear regression between 1.0 M HCl and pH to determine the volume of acid to add. The milk was stored in the cold room overnight. Milk pH adjustment after $CaCl_2$ addition ensured that any observed effect of calcium level on dependent variables was not due to an indirect effect of $CaCl_2$ on milk pH.

On the day of coagulation trials the milk was adjusted to a final pH of 6.5 at 2° C. using 1.0 M HCl. A constant dilution rate was assured by adding de-ionized water for a total added volume of HCl plus de-ionized water of 60 mL. Milk was slowly heated to the coagulation temperature ±0.15° C., to minimize the impact of the temperature change on casein micelle equilibrium. Seven kg of the heated milk were added to the vat and left to equilibrate until thermal equilibrium was achieved. Coagulation temperature was controlled using a single jacket cheese vat supplied with temperature controlled water through a copper-coil connected to a water bath having a control accuracy of ±0.01° C. (Lauda, RM 20, Brinkman Instrument Inc., Westbury, N.Y., USA). Milk temperature was measured with a precision thermistor (model 5831 A, Omega Engineering, Stanford, Conn., resolution ±0.01° C.; accuracy ±0.2° C.). The enzyme used for milk coagulation was chymosin (CHY-MAX® Extra; EC 3.4.23.4 isozyme B, 643 IMCU $mL^{-1}$; Chr. Hansen Inc., Milwaukee, Wis., USA). Once thermal equilibrium was achieved Chymosin was added to the milk in the vat at a level of 0.06 mL $kg^{-1}$ milk. Data acquisition for optical sensors commenced upon addition of the enzyme i.e. time $t_{c(0)}$.

A CoAguLite™ (CL) sensor (Model 5, Reflectronics Inc., Lexington, Ky., USA; U.S. Pat. No. 5,172,193) was employed to select the different experimental levels of cutting time during coagulation, and also as a reference light backscatter sensor to which the signal from the LFV (Example 1) could be compared. This sensor transmitted near infrared light at 880 nm through two 600 μm diameter fibers. One fiber transmitted infrared radiation into the milk sample while the other fiber transmitted the radiation scattered by the milk particles to a silicon photo-detector. For calibration, the CL sensor was zeroed by excluding light and adjusting the output voltage to 1 V. The sensor gain was calibrated to give a 2 V signal response when placed in the milk sample. Response data were collected every 6 s. It is noted that parameters in the text and or tables herein superscripted with an asterisk denote that they were calculated from the CL sensor response, as differentiated from those obtained from the LFV sensor. The initial voltage response ($V^*_0$) was calculated by averaging the first ten data points after correction for the 1 V offset. A light backscatter ratio (R*) was calculated by dividing the sensor output voltage at any time (less the 1 V output) by $V^*_0$. The first derivative (R'*) of the light backscatter ratio profile was calculated by conducting linear least-squares regression on the most recently collected 4 min of data. The calculated slope was assigned to the midpoint of the data subset used. The second derivative (R"*) was calculated in a similar manner but using 60 data points to smooth the R"* profile.

Light backscatter response from both sensors was continuously monitored from the time of rennet addition ($t_{co}$) to the end of syneresis ($t_{s85}$). Experimental cutting time levels were selected by light backscatter measurements using the CL sensor as described below. The CL sensor also provided a reference light backscatter measurement to which the LFV sensor response could be compared in order to determine the LFV sensors ability to monitor coagulation and syneresis. A number of light backscatter parameters were derived from both the LFV and CL sensor response during coagulation and syneresis. The light backscatter parameters are defined in Table 2. The optical parameters derived from the light backscatter profiles during coagulation can be classified as time-based, response-based or mixed-based parameters (Table 2).

TABLE 2

Definition of optical parameters derived from the light backscatter ratio profiles during coagulation and syneresis.

| Parameter | Units | Definition[a] |
|---|---|---|
| $t_{max}$ | min | Time to the first maximum of R' |
| $t_{cut}$ | min | Time to gel cutting |
| $t_{2max}$ | min | Time to the first maximum of R" |
| $t_{2min}$ | min | Time to the first minimum of R" |

TABLE 2-continued

Definition of optical parameters derived from the light backscatter ratio profiles during coagulation and syneresis.

| Parameter | Units | Definition[a] |
|---|---|---|
| $R_{max}$ | dimensionless | Value of R at $t_{max}$ |
| $R_{2max}$ | dimensionless | Value of R at $t_{2max}$ |
| $R_{2min}$ | dimensionless | Value of R at $t_{2min}$ |
| $R_{cut}$ | dimensionless | Value of R at $t_{cut}$ |
| $R'_{max}$ | min$^{-1}$ | Value of R' at $t_{max}$ |
| $R''_{max}$ | min$^{-2}$ | Value of R'' at $t_{max}$ |
| $\Delta R_{coag}$ | Percent (%) | Percent increase in R from $t_{c(o)}$ to $t_{c(cut)}$ |
| $\Delta R_{syn}$ | Percent (%) | Percent decrease in R from $t_{s(o)}$ to $t_{s(85)}$ |

[a]R = light backscatter ratio; R' = 1$^{st}$ derivative of the light backscatter ratio R'' = 2$^{nd}$ derivative light backscatter ratio; $t_{c(o)}$ = time of enzyme addition; $t_{c(cut)}$ = end of coagulation; $t_{s(o)}$ = start of syneresis. $t_{s(85)}$ = end of syneresis.

Experimental cutting times used in each experiment were selected based on measurements of light backscatter using the CL sensor. The CL sensor gave a real time target value for $t_{cut}$ for each experiment using the following prediction equation:

$$t^*_{cut} = \beta t^*_{max} \quad (1)$$

where $t^*_{max}$ was the first maximum of $R'^*_{max}$, and $\beta$ was a constant. A number of different $\beta$ values (1.3, 1.8, 9.5, 3.2, and 3.7) obtained in compliance with the experimental design shown in Table 1 were used to establish the range of target $t^*_{cut}$ values for the experiment.

When optimum cutting time was indicated by the CL data acquisition software, the gel was cut by pushing a cutting knife vertically through the gel. This cut the gel into prismatic columns. The knife was then rotated once ensuring all the gel was cut into cubes of approximately 1 cm$^3$. The last recorded time point prior to cutting is designated $t_{c(cut)}$, with the next time point defined as the start of the syneresis process ($t_{s(0)}$). The curd was left to heal for 4.5 min before stirring at 10±0.02 rpm was initiated (Servodyne mixer 50003-10, Cole Parmer Instrument Co. IL, USA). The stirring process continued at this speed up to 85 min ($t_{s(85)}$).

Sampling and compositional analysis of curd and whey was carried out using reported procedures [Fagan, C. C.; Leedy, M.; Castillo, M.; Payne, F. A.; O'Donnell, C. P.; O'Callaghan, D. J., Development of a light scatter sensor technology for on-line monitoring of milk coagulation and whey separation. *J. Food Eng.* 83 (2007): 61-67]. Samples of curd and whey were removed for compositional analysis at $t_{s(5)}$ and every 10 min thereafter up to $t_{s(85)}$ (i.e. 9 samples). Curd and whey was separated using a sieve (75 μm pore size). 3 g of curd and 5 g of whey were weighed into dishes using an analytical balance. The dishes were dried in a convection oven at 102° C., until they reached a constant weight (~15 h). Samples were analyzed in triplicate. Chemical composition of whey was also determined using the MilkoScan FT120. Compositional analysis of the milk showed that there were minimal differences between batches. The average composition of the milk ± the standard deviation (SD) was 3.7±0.3%, 3.5±0.1% and 12.2±0.3% for fat, protein and total solids contents respectively.

A number of authors have observed that during syneresis, whey separation and curd shrinkage followed first order kinetics. Therefore the following first order equation was fitted to the curd moisture experimental data during syneresis:

$$CM_t = CM_\infty + (CM_0 - CM_\infty)e^{-kCMt} \quad (2)$$

where $CM_t$ was the curd moisture (%) at time t (min), $CM_\infty$ represented the curd moisture (%) at an infinite time, $CM_0$ was the curd moisture content (%) at the beginning of syneresis, $t_{s(0)}$, i.e. the milk moisture content, and $k_{CM}$ was the kinetic rate constant (min$^{-1}$) for curd moisture content changes during syneresis. Procedure NLIN in SAS was used to determine the parameters $CM_\infty$ and $k_{CM}$, while $CM_0$ was set at the known value for the milk moisture content in each experiment.

Whey fat concentration in the vat has been found to follow a first order response. Similarly, temperature affects whey fat release during syneresis. At temperatures below 37° C. whey fat concentration decreased during syneresis, but at 37° C. or higher whey fat concentration increased during syneresis. Therefore two equations were required to characterize the change in whey fat concentration during syneresis. At temperatures below 37° C. whey fat concentration was fitted to a first order decreasing equation:

$$WF_t = WF_\infty + (WF_5 - WF_\infty)e^{-kWFt}, \quad (3)$$

while at temperatures of 37° C. or higher a first order increasing equation was used:

$$WF_t = WF_5 + (WF_\infty - WF_5)(1 - e^{-kWFt}), \quad (4)$$

where $WF_T$ was the whey fat concentration (%) at time t (min), $WF_\infty$ represented the whey fat content (%) at an infinite time, $WF_5$ was the whey fat content (%) five minutes after cutting time, $t_{s(5)}$, and $k_{WF}$ was the kinetic rate constant (min$^{-1}$) for whey fat concentration changes during syneresis (using the term whey fat dilution to describe the changes of whey fat concentration during syneresis). Procedure NLIN was used to predict the parameters $WF_\infty$, $WF_5$ and $k_{WF}$.

It was expected that for the signal from the LFV sensor to be related to curd moisture or whey fat concentration or both, the signal should follow first order kinetics for most conditions, except for high temperature conditions, where the signal may reflect the particular effect of temperature on whey fat content. Therefore the LFV sensor response during syneresis was also fitted to a first order equation as follows:

$$R_t = R_\infty + (R_0 - R_\infty)e^{-kLFVt}, \quad (5)$$

where $R_t$ was the light backscatter ratio at time t (min), $R_\infty$ represented the light backscatter ratio at an infinite time, $R_0$ was the light backscatter ratio at $t_{s(0)}$, and $k_{LFV}$ was the kinetic rate constant (min$^{-1}$) for the LFV sensor response during syneresis. Procedure NLIN was used to predict the parameters $R_\infty$, $R_0$ and $k_{LFV}$.

Figure 2:
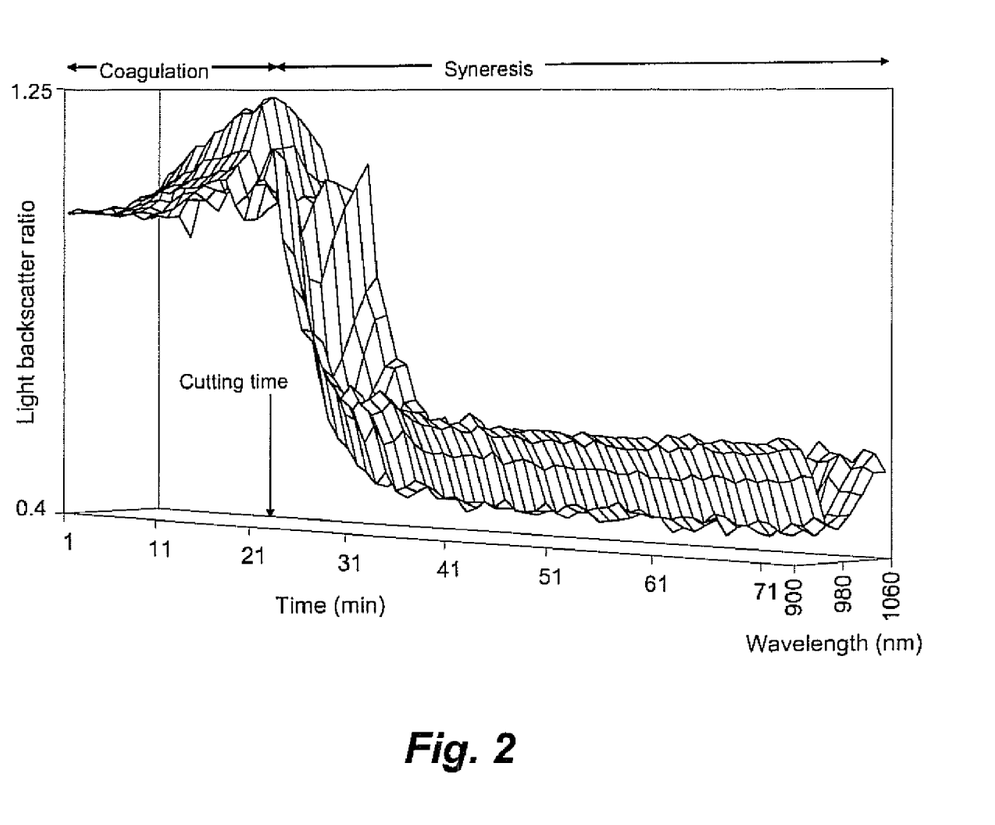
FIG. 2 illustrates a representative LFV sensor response (average of 3 replicates) during coagulation and syneresis (temperature=32° C.; $CaCl_2$=2 mM) at wavelengths between 900 and 1060 nm, with time measured from rennet addition (time=0 min)

A typical light backscatter profile derived from the LFV sensor during coagulation and syneresis at wavelengths between 900 and 1060 nm is shown in FIG. 2. Enzyme was added at time zero and the light backscatter ratio (ratio of light backscatter sensor signal to light backscatter sensor signal at time zero) was calculated. The coagulation phase ended and the syneresis phase began at a process time in the range 10 to 50 min (~18 minutes in FIG. 4) when the gel was cut. During coagulation the light backscatter ratio increased, and the LFV sensor response was greatest at 980 nm as indicated by the peak at this wavelength observed throughout coagulation (FIG. 2). With the onset of syneresis following cutting of the gel, the signal decreased exponentially over time. FIG. 2 also shows that the LFV sensor response during syneresis was further characterized by a valley at 980 nm. This trend, of a maximum increase during coagulation and the maximum decrease during syneresis at 980 nm, was consistently observed for all experimental conditions. For all conditions the average increase during coagulation at 980 nm was 20.5±5.8% (mean±SD), while during syneresis the average decrease was 59.4±12.0% (mean±SD). Generally the LFV sensor signal also incorporated less noise at 980 nm than at other wavelengths. On this basis the following analysis of the LFV sensor response has been carried out at 980 nm.

Figure 3:
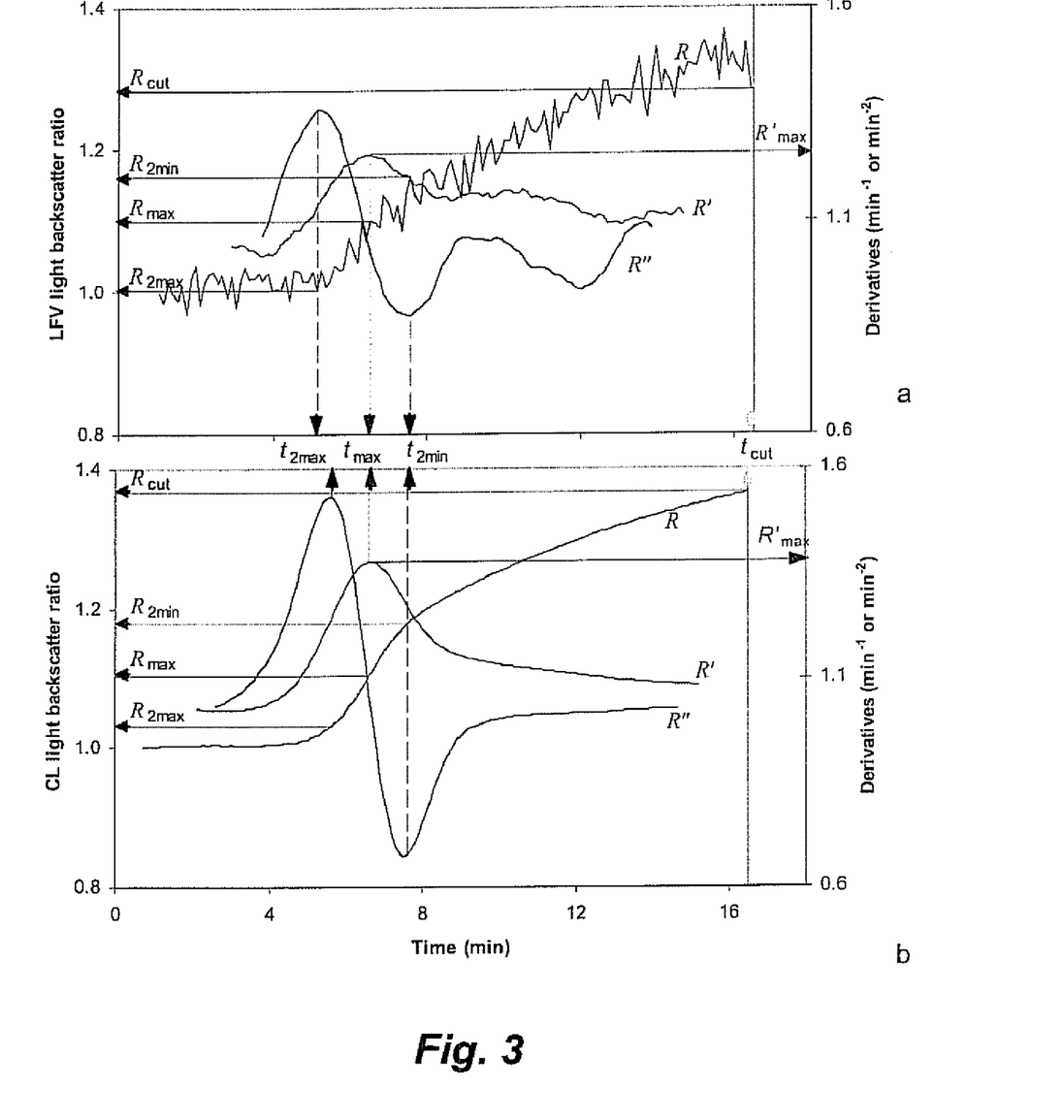
FIGS. 3a and 3b illustrate light backscatter ratio profiles and their characteristic first and second derivatives versus time for the (a) LFV sensor and (b) CL sensor (temperature=32° C., $\beta$=2.5, $CaCl_2$=2 mM))

In order to determine if the LFV sensor was comparable to the CL sensor for monitoring coagulation, optical parameters, as defined in Table 2, were derived from the LFV and CL light backscatter ratio profiles during coagulation. FIG. 3 shows the LFV and CL response to coagulation and their respective derivatives. It is clear the LFV sensor response contains a high degree of scatter, which could present a difficulty in calculating important parameters such as $t_{max}$. Despite the degree of noise in the light backscatter ratio, R, it was still possible to successfully calculate R' and R" and derive the same time, response, and mixed based parameters that were derived from the CL sensor response and which can be used to characterize coagulation. Correlations between the CL and LFV derived parameters are shown in Table 3.

The light backscatter ratio during the coagulation phase was measured between 400 and 1200 nm for the test conducted. The increase in light backscatter ratio, $\Delta R_{coag}$, was found to be maximal at 980 nm. The average increase was 20.5±5.8%. Accordingly, subsequent experiments were conducted using light emitted at 980 nm.

Figure 4:
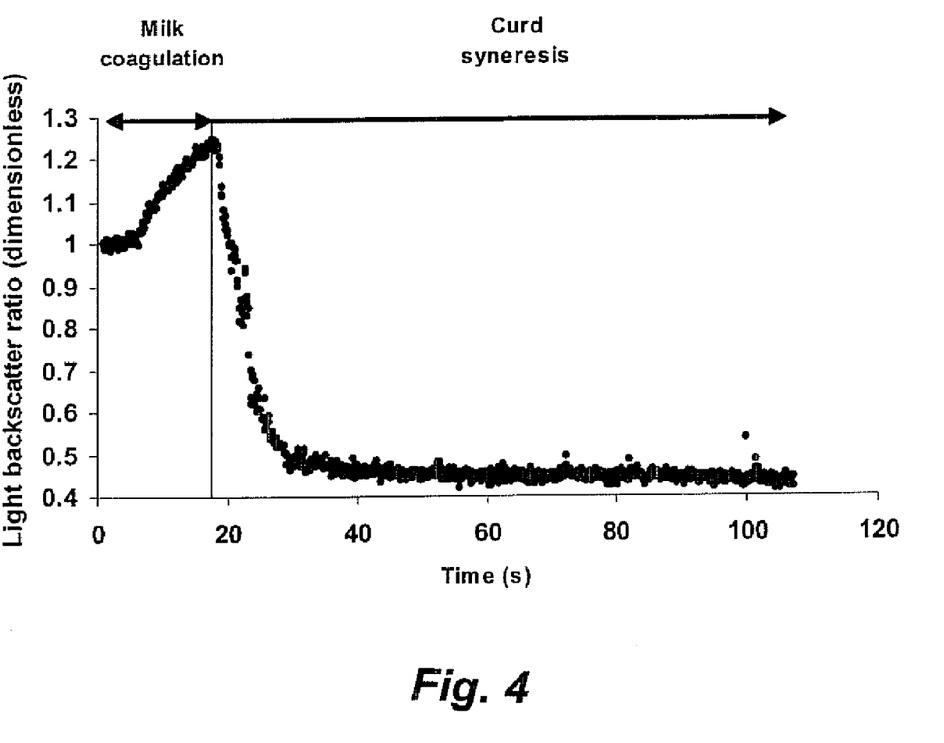
FIG. 4 illustrates a representative LFV sensor response during coagulation and syneresis (temperature=32° C.; $CaCl_2$=2 mM) at 980 nm.

The syneresis phase starts with the gel cutting (process time of ~18 minutes, light emitted at 980 nm; see FIG. 4). The light backscatter ratio, R, decreased exponentially with time following gel cutting and was described by the following equation:

$$R_t = R_\infty + (R_0 - R_\infty)e^{-kt} \tag{6}$$

TABLE 3

Pearson correlation coefficients (r) and significance$^a$ between parameters derived from the LFV and CL sensors coagulation profile.

| | $t_{2max}$ | $t_{2min}$ | $R_{max}$ | $R'_{max}$ | $t^*_{max}$ | $t^*_{2max}$ | $t^*_{2min}$ | $R^*_{max}$ | $R'^*_{max}$ |
|---|---|---|---|---|---|---|---|---|---|
| $t_{max}$ | 0.97*** | 0.98*** | −0.41** | −0.89*** | 0.99*** | 0.99*** | 0.99*** | −0.76*** | −0.89*** |
| $t_{2max}$ | 1 | 0.96*** | −0.44*** | −0.89*** | 0.97*** | 0.96*** | 0.97*** | −0.76*** | −0.90*** |
| $t_{2min}$ | | 1 | −0.38** | −0.83*** | 0.99*** | 0.97*** | 0.99*** | −0.68*** | −0.83*** |
| $R_{max}$ | | | 1 | 0.63*** | −0.46*** | −0.47*** | −0.46*** | 0.63*** | 0.62*** |
| $R'_{max}$ | | | | 1 | −0.89*** | −0.92*** | −0.89*** | 0.89*** | 0.97*** |
| $t^*_{max}$ | | | | | 1 | 0.99*** | 1.00*** | −0.76*** | −0.89*** |
| $t^*_{2max}$ | | | | | | 1 | 0.99*** | −0.79*** | −0.92*** |
| $t^*_{2min}$ | | | | | | | 1 | −0.76*** | 0.90*** |
| $R^*_{max}$ | | | | | | | | 1 | 0.94*** |

$^a$Significance:
***P < 0.001;
**P < 0.01;
N = 60.

These results demonstrate the close relationship between the CL and LFV derived parameters obtained during milk coagulation. All LFV derived parameters were significantly correlated with CL derived parameters. In particular the LFV parameters, $t_{max}$, $t_{2max}$, $t_{2min}$, and $R'_{max}$ were very significantly correlated with their CL derived counterparts (correlation coefficient (r)=0.99–0.96, P≦0.001). Considering the level of scattering in R the correlation between $R_{max}$ and $R^*_{max}$ are still reasonable and significant (r=0.63, P<0.001). The parameters $t_{max}$, $R'_{max}$ were dependent on coagulation rate and, as expected, were found to be significantly and negatively correlated (r=−0.89, P<0.001).

These results showed also that the LFV sensor, which has a wider field of view, is sensitive, like the CL sensor, to both aggregation of casein micelles and the development of curd firmness. Therefore the LFV sensor can monitor milk coagulation and predict optimal gel cutting time at least as well as already-proven technology (the CL sensor).

The light backscatter ratio during the milk coagulation step contained three phases: latent, sigmoidal, and exponential. These are substantially as described in U.S. Pat. No. 5,172,193 to Payne et al. The parameters obtained from the light backscatter profile during the coagulation step are shown in FIG. 3, and defined as follows:

$t_{max}$=the time between adding the enzyme and the occurrence of the maximum rate of change in the light backscatter ratio, minutes, $R_{max}$=value of R at $t_{max}$, dimensionless, $\Delta R_{coag}$=increase in R during milk coagulation, percent, R'=the slope of R with respect to time, min$^{-1}$, $R'_{max}$=value of R' at $t_{max}$, min$^{-1}$.

where $R_0$=light backscatter ratio at time zero for the syneresis step (when the gel is cut syneresis time is zero), dimensionless, $R_t$=light backscatter ratio at time t after gel cutting, dimensionless, $R_\infty$=light backscatter ratio at an infinite time after gel cutting, dimensionless t=time, min, k=kinetic rate constant estimated from the light backscatter sensor response for the syneresis phase, min$^{-1}$.

The decrease in light backscatter ratio during curd syneresis, $\Delta R_{syn}$ (% decrease in R), was found to be a maximum for infrared light at a wavelength of 980 nm (FIG. 4). The average $\Delta R_{syn}$ value was 59.4±12.0%. The observation of a maximum increase during coagulation and the maximum decrease during syneresis was consistently observed at 980 nm for all experimental conditions tested.

It was observed that the changes in R during syneresis were a response to curd shrinkage or compositional changes in whey fat content and followed a first order reaction. The experimental data were fitted with a first order equation for modelling the changes in curd moisture, whey fat concentration, and light backscatter ratio. The following rate constants were determined:

k=kinetic rate constant estimated from the light backscatter sensor response for the syneresis phase, min$^{-1}$, $k_{CM}$=kinetic rate constant estimated from the curd moisture changes during the syneresis phase, min$^{-1}$, $k_{IVF}$=kinetic rate constant estimated from the whey fat changes during the syneresis phase, min$^{-1}$.

Regression analysis showed that the changes in these three variables during syneresis followed first order kinetics. The optically derived kinetic rate constant, k, was found to be significantly related to both coagulation and syneresis parameters, but most importantly, k was significantly and positively correlated with $k_{CM}$ (P<0.001, r=0.84) and $k_{WF}$ (P<0.01, r=0.42). These results indicated that the response of the LFV sensor during syneresis was related to changes in curd moisture content and whey fat content. These data confirmed that LFV sensor response (via the optically derived kinetic rate constant, k) could be used for monitoring syneresis and predict changes in curd moisture and whey fat content. In addition, since $k_{CM}$ and $k_{WF}$ are correlated the measurement of the kinetics of whey fat dilution may also be used to monitor syneresis and predict changes in curd moisture content. Thus, fat globule dilution was factored in as a natural tracer of syneresis.

During a syneresis process the value of k needs to be determined as early as possible to allow time for endpoint prediction. This is because the endpoint of syneresis occurs at the desired curd moisture content. To achieve this early determination, the first order equation (Eqn. 5 above) was fit to the first 15 minutes of light backscatter data collected after gel cutting to give the kinetic constant $k_{15}$. Advantageously, this allowed utilizing the method of the present invention to provide a prediction of the syneresis endpoint after only 15 minutes into the syneresis process step.

Fat losses in the whey, final curd moisture content and final curd yield are important cheese making measurements that significantly impact on final product quality. These measurements were predicted using parameters generated from the light backscatter profiles ($t_{max}$, $R_0$, $R_\infty$, $k_{15}$), the properties of the milk (P, F, TS, FP), and the operating conditions (T), where:

T=temperature (° C.)
P=milk protein (%)
F=milk fat (%)
FP=milk fat to protein ratio, dimensionless
TS=milk total solids (%)
$\beta_i$=regression coefficients The best models for prediction of total whey fat losses (WF) final curd yield on a wet basis (CY), final curd moisture content (CM) at the end of the process (t=85 min) and for estimation of the kinetic rate constant for curd moisture changes during syneresis ($k_{CM}$), using LFV light backscatter parameters, are shown in Table 4.

TABLE 4

Models for prediction of total whey fat losses, final curd yield, final curd moisture content and the kinetic rate constant for curd moisture changes during syneresis using LFV light backscatter parameters.

| | Model | $R^2$ | SEP |
|---|---|---|---|
| I | WF = $\beta_0 + \beta_1 T + \beta_2 T^2 + \beta_3 P + \beta_4 R_\infty$ | 0.93 | 2.646 g |
| II | CY = $\beta_0 + \beta_1 T + \beta_2 T^2 + \beta_3 TS + \beta_4 R_0$ | 0.90 | 0.950% |
| III | CM = $\beta_0 + \beta_1 T + \beta_2 t_{max} + \beta_3 F + \beta_4 FP$ | 0.94 | 1.456% |
| IV | $k_{CM} = \beta_0 + \beta_1 T^2 + \beta_2 t_{max} + \beta_3 k_{15}$ | 0.52 | 0.031 min$^{-1}$ |

A curd moisture content prediction model was developed to predict curd moisture during syneresis as a function of time by using a combination of milk temperature, milk composition parameters and LFV dependent variables ($t_{max}$, $R_\infty$, $R_0$, and $k_{15}$). The curd moisture prediction model was:

$$CM(t) = CM_\infty + (CM_0 - CM_\infty)\exp(-k_{CM}t) \quad (7)$$

where
$CM_0$=curd moisture content (%) at the beginning of syneresis. This is the moisture content of milk and a known parameter,
CM(t)=curd moisture (%) during syneresis at time t after gel cutting (min),
$CM_\infty$=curd moisture (%) at an infinite time,
$k_{CM}$=kinetic rate constant (min$^{-1}$) for curd moisture content changes during syneresis.

The two unknowns in equation 6 are $CM_\infty$ and $k_{CM}$. The value for $k_{CM}$ was determined using Model IV (Table 4). The value of $CM_\infty$ was estimated using Model III (Table 4). These substitutions into equation 7 defined a curd moisture content prediction model (Model V) which was:

$$CM(t) = \beta_0 + \beta_1 T + \beta_2 t_{max} + \beta_3 F + \beta_4 FP + (CM_0 - (\beta_0 + \beta_1 T + \beta_2 t_{max} + \beta_3 F + \beta_4 FP))\exp((-\beta_5 T^2 + \beta_6 t_{max} + \beta_7 k_{15})t) \quad (8)$$

Figure 5:
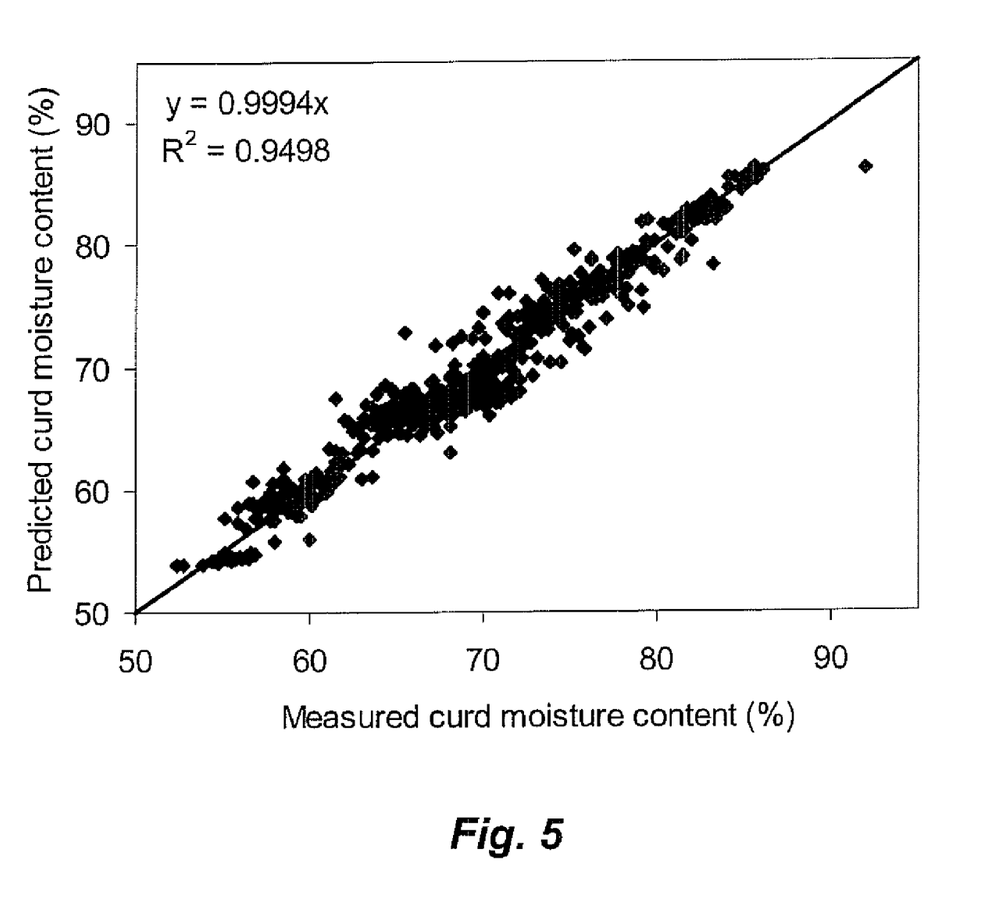
FIG. 5 compares predicted vs. measured curd moisture content obtained using a model set forth in the present description as Model V.

The prediction of curd moisture content as a function of time was then possible by fitting this Model V to the curd moisture content data collected during the testing. The observed and predicted curd moisture contents are shown in FIG. 5. This model had an $R^2$ of 0.95 and an SEP of 1.72%. The prediction used 540 data points within a wide range of moisture contents from 50 to 90%.

The skilled artisan will readily appreciate that all the predictors used in models I to IV and those used in model V are known as early as 15 min after cutting the gel. Accordingly, the present invention provides a real time model to predict curd moisture as a function of time after $k_{15}$ is determined. In this fashion, syneresis endpoint, that is, the desired curd moisture content in accordance with the type of cheese being made, can be accurately predicted and the syneresis phase of the cheese making process optimized.

The processes of coagulation and syneresis during cheese making can therefore be monitored, endpoints predicted, and controlled using the present technology, that is, using a single sensor and method. The LFV sensor technology offers potential for in-vat control of both the milk coagulation and syneresis steps in cheese making in a stirred cheese vat. Thus, the present method allows precise prediction, using the same optical technology, of both optimal milk coagulum cutting time and curd syneresis endpoint and therefore optimization of curd moisture content. Using the present method, both optimal cutting time control and the syneresis endpoint control based on desired curd moisture content may be established by in-line monitoring during the cheese making process, allowing the process to be substantially automated. That is, by use of the present technology, it is now possible to monitor and optimise processing parameters, using the same monitoring technology, in a mixture that varies from a substantially homogenous dispersion (milk) to a biphasic mixture comprising a solid and a liquid (the curd and whey mixture) which is constantly changing in moisture, solid:liquid ratio, and optical parameters. A simple, reliable method is thereby provided for optimizing cheese making parameters during the first, critical stages of the cheese making process. Information gathered during the practice of the process of the present invention, including whey fat concentration and cheese yield, will also allow the cheese making process to be optimized based on economics.

The present method is applicable to the making of low, medium, and high moisture cheeses. Further, the method provides cost savings in that the cheese producer is provided a mechanism to avoid unnecessary syneresis processing in the cheese making vat, and also allowing the cheese maker to alter curd size as milk solid content changes during the course of a year. Still further, the method of the present invention allows real-time in-line monitoring of, and on-site application of or adjustment to, necessary process changes in the cheese making process to obtain a predetermined curd moisture content even if starter culture inhibition occurs, such as from bacteriophage infection or agglutination problems. By use of the method of the present invention, comprehensive process control of cheese making in the vat, and for predicting curd moisture content, is provided.

The foregoing description of preferred embodiments has been presented for purposes of illustration and description. It is not intended to be exhaustive or limiting to the invention to the precise forms disclosed. Obvious modifications or variations are possible in light of the above teachings. The embodiments were chosen and described to provide the best illustration of the principles described herein and their practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled. All patents, patent applications, and non-patent references cited in the present disclosure are incorporated into the present disclosure in their entirety by reference.

What is claimed is:

1. In a cheese making process, a method of improving quality of cheese produced from a milk batch, comprising:
   impinging a light beam from an incident light source onto a surface of said milk batch;
   optically detecting light backscattered from said milk batch during a coagulation process to collect light backscatter data and correlating that light backscatter data to an optimum cutting time whereby a syneresis process is initiated;
   optically detecting light backscattered from a biphasic curd and whey mixture derived from said milk batch during the syneresis process to collect light backscatter data; and
   predicting an optimum syneresis endpoint using the collected light backscatter data of the biphasic curd and whey mixture.

2. The method of claim 1, including predicting said optimum syneresis endpoint by correlating at least one of said backscattered light data, optical parameters developed from analysis of the backscattered light data, and whey fat dilution to at least one of a milk protein %, a milk fat %, a milk total solids content, a milk processing temperature, a curd moisture content, a curd moisture change over time, whey fat content, a whey fat loss, and a final curd yield.

3. The method of claim 1, including using an equation for analyzing said light backscatter data to provide a curd moisture parameter predictive of an optimum syneresis process endpoint, said equation comprising:

$$CM(t)=\beta_0+\beta_1 T+\beta_2 t_{max}+\beta_3 F+\beta_4 FP+(CM_0-(\beta_0+\beta_1 T+\beta_2 t_{max}+\beta_3 F+\beta_4 FP))\exp((-\beta_5 T^2+\beta_6 t_{max}+\beta_7 k_{15})t)$$

where
$CM_0$=curd moisture content (%) at the beginning of syneresis;
$CM(t)$=curd moisture (%) during syneresis at time t after gel cutting (min);
$CM_\infty$=curd moisture (%) at an infinite time;
$k_{CM}$=kinetic rate constant (min$^{-1}$) for curd moisture content changes during syneresis;
T=temperature (° C.);
P=milk protein (%);
F=milk fat (%);
FP=milk fat to protein ratio (dimensionless);
TS=milk total solids (%); and
$\beta_i$=regression coefficients.

4. The method of claim 1, wherein the light source emits light at a wavelength of from about 950 nm to about 1000 nm.

5. The method of claim 3, wherein the equation is predictive of an optimum syneresis endpoint after collection of light backscatter data for about 15 minutes following said cutting step for initiating syneresis.

6. The method of claim 1, wherein said steps of impinging the light beam, optically detecting light backscattered from said milk batch during the coagulation process, and optically detecting light backscattered from said milk batch during the syneresis process are accomplished by:
   providing a light guide for guiding the light beam onto the milk batch surface, said light guide having a diameter of about 0.2 inches; and
   providing a light collector for collecting backscattered light reflected from the milk batch surface and transmitting that collected backscattered light to an optical detector, said light collector having a diameter of about 0.2 inches;
   wherein the light guide and the light collector are separated by a distance of about 0.4 inches to about 0.6 inches.

7. The method of claim 6, wherein the optical detector is selected from a group of devices consisting of a fiber optic spectrometer, a colorimeter, a CCD camera, a photo detector, and combinations thereof.

8. A method of predicting an optimum endpoint for a syneresis process in a cheese making process, comprising:
   impinging a light beam from an incident light source onto a surface of a biphasic curd and whey mixture derived from a milk batch;
   optically detecting light backscattered from said curd and whey mixture during the syneresis process to collect light backscatter data; and
   predicting an optimum syneresis endpoint using the collected light backscatter data.

9. The method of claim 8, including including said optimum syneresis endpoint by correlating at least one of said backscattered light data, optical parameters developed from analysis of the backscattered light data, and whey fat dilution to at least one of a milk protein %, a milk fat %, a milk total solids content, a milk processing temperature, a curd moisture content, a curd moisture change over time, whey fat content, a whey fat loss, and a final curd yield.

10. The method of claim 8, including using an equation for analyzing said light backscatter data to provide a curd moisture parameter predictive of an optimum syneresis process endpoint, said equation comprising:

$$CM(t)=\beta_0+\beta_1 T+\beta_2 t_{max}+\beta_3 F+\beta_4 FP+(CM_0-(\beta_0+\beta_1 T+\beta_2 t_{max}+\beta_3 F+\beta_4 FP))\exp((-\beta_5 T^2+\beta_6 t_{max}+\beta_7 k_{15})t)$$

where
$CM_0$=curd moisture content (%) at thgge beginning of syneresis;
$CM(t)$=curd moisture (%) during syneresis at time t after gel cutting (min);
$CM_\infty$=curd moisture (%) at an infinite time;
$k_{CM}$=kinetic rate constant (min$^{-1}$) for curd moisture content changes during syneresis;
T=temperature (IC);
P=milk protein (%);
F=milk fat (%);
FP=milk fat to protein ratio (dimensionless);

TS=milk total solids (%); and
$\beta_i$=regression coefficients.

11. The method of claim 8, wherein the light source emits light at a wavelength of from about 950 nm to about 1000 nm.

12. The method of claim 10, wherein the equation is predictive of an optimum syneresis endpoint after collection of light backscatter data for about 15 minutes following a cutting step which initiates the syneresis process.

13. The method of claim 8, wherein said steps of impinging the light beam and optically detecting light backscattered from said curd and whey mixture during the syneresis process are accomplished by:
  providing a light guide for guiding the light beam onto the curd and whey mixture surface, said light guide having a diameter of about 0.2 inches; and
  providing a light collector for collecting backscattered light reflected from the curd and whey mixture surface and transmitting that collected backscattered light to an optical detector, said light collector having a diameter of about 0.2 inches;
  wherein the light guide and the light collector are separated by a distance of about 0.4 inches to about 0.6 inches.

14. The method of claim 13, wherein the wherein the optical detector is selected from a group of devices consisting of a fiber optic spectrometer, a colorimeter, a CCD camera, a photo detector, and combinations thereof.

15. In a cheese making process, a method of improving quality of cheese produced from a milk batch, comprising:
  impinging a light beam from an incident light source onto a surface of said milk batch;
  optically detecting light backscattered from said milk batch during a coagulation process to collect light backscatter data and correlating that light backscatter data to an optimum cutting time whereby a syneresis process is initiated; and
  optically detecting light backscattered from a biphasic curd and whey mixture derived from said milk batch during the syneresis process to collect light backscatter data and correlating that light backscatter data to an optimum syneresis endpoint;
  wherein said light backscatter data is analysed to provide a curd moisture parameter predictive of an optimum syneresis process endpoint according to an equation:

$$CM(t)=\beta_0+\beta_1 T+\beta_2 t_{max}+\beta_3 F+\beta_4 FP+(CM_0-(\beta_0+\beta_1 T+\beta_2 t_{max}+\beta_3 F+\beta_4 FP))\exp((-\beta_5 T^2+\beta_6 t_{max}+\beta_7 k_{15})t)$$

where
  $CM_0$ =curd moisture content (%) at the beginning of syneresis;
  $CM(t)$=curd moisture (%) during syneresis at time t after gel cutting (min);
  $CM_\infty$=curd moisture (%) at an infinite time;
  $k_{CM}$=kinetic rate constant (min$^{-1}$) for curd moisture content changes during syneresis;
  T=temperature (° C);
  P=milk protein (%);
  F=milk fat (%);
  FP=milk fat to protein ratio (dimensionless);
  TS=milk total solids (%); and
  $\beta_i$=regression coefficients.

16. A method of predicting an optimum endpoint for a syneresis process in a cheese making process, comprising:
  impinging a light beam from an incident light source onto a surface of a biphasic curd and whey mixture derived from a milk batch; and
  optically detecting light backscattered from said curd and whey mixture during the syneresis process to collect light backscatter data and correlating that light backscatter data to an optimum syneresis endpoint;
  wherein said light backscatter data is analysed to provide a curd moisture parameter predictive of an optimum syneresis process endpoint according to an equation:

$$CM(t)=\beta_0+\beta_1 T+\beta_2 t_{max}+\beta_3 F+\beta_4 FP+(CM_0-(\beta_0+\beta_1 T+\beta_2 t_{max}+\beta_3 F+\beta_4 FP))\exp((-\beta_5 T^2+\beta_6 t_{max}+\beta_7 k_{15})t)$$

where
  $CM_0$=curd moisture content (%) at the beginning of syneresis;
  $CM(t)$=curd moisture (%) during syneresis at time t after gel cutting (min);
  $CM_\infty$=curd moisture (%) at an infinite time;
  $k_{CM}$=kinetic rate constant (min$^{-1}$) for curd moisture content changes during syneresis;
  T=temperature (° C);
  P=milk protein (%);
  F=milk fat (%);
  FP=milk fat to protein ratio (dimensionless);
  TS=milk total solids (%); and
$\beta_i$=regression coefficients.

* * * * *

UNITED STATES PATENT AND TRADEMARK OFFICE
CERTIFICATE OF CORRECTION

| | | |
|---|---|---|
| PATENT NO. | : 7,892,584 B2 | Page 1 of 1 |
| APPLICATION NO. | : 12/109650 | |
| DATED | : February 22, 2011 | |
| INVENTOR(S) | : Castillo et al. | |

It is certified that error appears in the above-identified patent and that said Letters Patent is hereby corrected as shown below:

Claim 9, column 14, line 41, please replace "including" (second use) with --predicting--.

Claim 10, column 14, line 63, please replace "(IC)" with --(° C)--.

Signed and Sealed this
Twenty-sixth Day of April, 2011

David J. Kappos
*Director of the United States Patent and Trademark Office*